(12) United States Patent
Mellbin (10) Patent No.: US 9,795,698 B2
(45) Date of Patent: Oct. 24, 2017

(54) POWER SUPPLY

(71) Applicant: TETRA LAVAL HOLDINGS & FINANCE S.A, Pully (CH)

(72) Inventor: Håkan Mellbin, Hörby (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 15/119,996

(22) PCT Filed: Jan. 21, 2015

(86) PCT No.: PCT/EP2015/051068
§ 371 (c)(1),
(2) Date: Jan. 30, 2017

(87) PCT Pub. No.: WO2015/124355
PCT Pub. Date: Aug. 27, 2015

(65) Prior Publication Data
US 2017/0065735 A1    Mar. 9, 2017

(30) Foreign Application Priority Data
Feb. 19, 2014    (SE) ........................................ 1450201

(51) Int. Cl.
*A61L 2/08*    (2006.01)
*A61L 2/20*    (2006.01)
(52) U.S. Cl.
CPC ............... *A61L 2/087* (2013.01); *A61L 2/208* (2013.01); *A61L 2202/23* (2013.01)

(58) Field of Classification Search
CPC ......... A61L 2/087; A61L 2202/23; A61L 2/08
(Continued)

(56) References Cited

U.S. PATENT DOCUMENTS 4,877,934 A * 10/1989 Spinello .................... A61L 2/04
219/68
6,558,537 B1 * 5/2003 Herrington ............ B01D 61/04
205/747

(Continued)

FOREIGN PATENT DOCUMENTS

DE    10 2011 056 628 A1    6/2013
WO    WO 2009/009681 A1    1/2009

OTHER PUBLICATIONS

International Search Report (PCT/ISA/210) issued on May 4, 2015, by the European Patent Office as the International Searching Authority for International Application No. PCT/EP2015/051068.

(Continued)

*Primary Examiner* — Nicole Ippolito
(74) *Attorney, Agent, or Firm* — Buchanan Ingersoll & Rooney PC (57) ABSTRACT

Power supply, in particular for a sterilization device, comprising a housing, wherein the housing comprises at least a first sector and a second sector, wherein the first sector comprises a first pair of opposing side walls, and wherein the second sector comprises a second pair of opposing side walls, wherein the side walls are orientated basically parallel to a vertical axis of the housing, wherein the first pair of side walls is arranged in a first angle and the second pair of side walls is arranged in a second angle, wherein the first angle and the second angle are different from each other.

17 Claims, 7 Drawing Sheets

(58) Field of Classification Search
USPC .......................... 250/453.11, 454.11, 455.11
See application file for complete search history.

(56) References Cited

U.S. PATENT DOCUMENTS

| | | |
|---|---|---|
| 2011/0012032 A1 | 1/2011 | Bufano et al. |
| 2012/0124941 A1 | 5/2012 | Mastio et al. |
| 2014/0369885 A1 | 12/2014 | Krueger |
| 2016/0074546 A1* | 3/2016 | Rizzone .................. A61L 2/10 |
| | | 250/455.11 |

OTHER PUBLICATIONS

Written Opinion (PCT/ISA/237) issued on May 4, 2015, by the European Patent Office as the International Searching Authority for International Application No. PCT/EP2015/051068.
Office Action issued Aug. 28, 2014, by the Swedish Patent Office in corresponding Swedish Patent Application No. 1450201-7.

* cited by examiner

POWER SUPPLY

This invention relates to a power supply, in particular for a sterilization unit, to a power supply device, in particular for a sterilization device, and to a sterilization unit, in particular for sterilization of packaging material.

In the prior art different devices and methods for sterilizing packaging materials are known. One method widely used in the prior art is sterilization by means of gases and in particular by means of hydrogen peroxide. However, efforts are being made to reduce the use of chemicals when sterilizing containers. Therefore, devices and methods have also become known which sterilize material by means of electron beams. In general, there is provided an electron beam emitter that is adapted to emit charge carriers, in particular electrons, wherein the packaging material can be sterilized by these charge carriers. In this context, power supplies are necessary to provide the high voltage that is used to operate the electron beam emitters that generate the charge carriers which enable the sterilization. Generally, a plurality of power supplies is arranged at a movable or rotatable, respectively, carousel or carrier plate. This involves different challenges. Since the carousel or carrier plate is movable, i.e. rotatable, the weight of the power supply and in particular of its housing should be as low as possible. In addition, the dimensions of the housing should be preferably small so that a large number of power supplies can be arranged within a small space. In particular, the housing should have a design that allows a flexible arrangement, i.e. an arrangement of a different number of power supplies. However, power supplies known from the prior art are too big, heavy and uncomfortable to use as they are often adapted and designed explicitly for one specific arrangement.

Therefore, it is an object of the current invention to provide a power supply, in particular for a sterilization unit, a power supply device, in particular for a sterilization device and a sterilization unit, in particular for sterilization of packaging material, which avoids the drawbacks of prior art and maintains low weight and high cost effectiveness in combination with best possible flexibility.

This object is achieved by a power supply according to claim 1, by a power supply device according to claim 7 and by a sterilization unit according to claim 10. Additional advantages and features of preferred embodiments of the current invention are defined in the dependent claims.

According to the invention, a power supply, in particular for a sterilization device, comprises a housing, wherein the housing comprises at least a first sector and a second sector, wherein the first sector comprises a first pair of opposing side walls, and wherein the second sector comprises a second pair of opposing side walls. The first pair of side walls is arranged in a first angle and the second pair of side walls is arranged in a second angle, wherein the first angle and the second angle are different from each other.

According to one or more embodiments of the invention the power supply is connectable or connected, respectively, to an electron beam emitter. Alternatively, also more than one electron beam emitter can be connected to one power supply. The combination of an electron beam emitter (or at least one) and the power supply is named sterilization unit. Generally, the connection is a form and/or force fit connection. The electron beam emitter comprises an electron generator for emitting charge carriers, such as electrons, along a path. The electron generator is generally enclosed in a hermetically sealed vacuum chamber. The vacuum chamber is provided according to one or more embodiments with an electron exit window. Furthermore, the electron generator comprises a cathode housing and a filament. In use, an electron beam is generated by heating the filament. When an electrical current is set through the filament, the electrical resistance of the filament causes the filament to be heated to a temperature in the order of 2.000° C. This heating causes the filament to emit a cloud of electrons. The electrons are accelerated towards the electron exit window by means of a high voltage potential between the cathode housing and the electron exit window. Subsequently, the electrons path through the electron exit window and continue towards a target area, e.g. a part of the packaging material that has to be sterilized. The high voltage potential is created by connecting the cathode housing and the filament to the power supply and by connecting the vacuum chamber to ground. The voltage that is supplied by the power supply lies, according to one or more embodiments, within a range of about 80 to 150 kV. However, higher and lower values are also possible.

An electron beam emitter as described before can be used for sterilization of packaging material, food, biological or medical devices and so on. There are no limitations concerning the content of the packaging material. Thus, the content can be liquid, semi-liquid or solid. There are also no limitations concerning the use of the sterilization device or the electron beam emitter itself, respectively. Thus, the electron beam emitter or the sterilization device, respectively, can be used for inside and/or outside sterilization of e.g. packaging material, such as packaging containers e.g. for food, liquids or drugs.

It is advantageous that the housing comprises the at least two sectors, wherein the first sector comprises the first pair of opposing side walls and wherein the second sector comprises the second pair of opposing side walls. The different angles of the side walls of the at least two sectors allow a specific design of the housing that is best possible adapted to an arrangement and or to dimensions of an electric system that is located within the housing. Thus, the sectioning of the housing into the at least two sectors allows a specific and exact adaptation of the outer dimensions of the housing. In other words, the housing can be formed as small as possible which advantageously reduces the cost of materials and also weight. However, no complicated design of the side walls is necessary which would increase the costs. According to one or more embodiments the side walls are basically flat or plane, respectively. The flexibility and cost effectiveness is achieved by the combination of the different sectors that have basically flat or plate side walls, wherein the side walls of the different sectors are arranged in different angles.

In one or more embodiments the first and second sectors are connected to each other in a transition region. The transition region can be formed e.g. as an edge or a radius/curve. Thus, a transition or intersection from the first to the second sector or from one sector to the next, in general, can be e.g. seamless or not. According to one or more embodiments the housing has a width (measured perpendicular to the plane of symmetry) in that transition region between the first and the second sector that lies within a range of about 70 to 300 mm. In one or more embodiments the range is about 70 to 150 mm. In one or more embodiments the electron beam emitter has a diameter of about 110 mm (at least that part of the electron beam emitter that is connected to the housing or the power supply, respectively) so that the width of the housing lays also expediently within a range of about 110 mm in the transition region. According to one or more embodiments, the housing comprises a plane of symmetry, wherein the plane of symmetry extends basically parallel to a vertical axis of the housing 23. The side walls 31, 32 are orientated basically parallel to said vertical axis A. The plane of symmetry is the basis for the measurement of the angles of the side walls. According to one or more embodiments the side walls of the sectors taper both towards the same direction. This means that the second angle is expediently bigger than the first angle, wherein the angle of the first pair of side walls is preferably not zero.

As already mentioned, the power supplies are generally arranged on a carousel or a carrier plate. Such a carousel or carrier plate is preferably round, in particular circular. Accordingly, the power supplies are arranged in a circle on the carousel or carrier plate. To optimize the arrangement, the side walls of the housing of the power supplies should be generally arranged as close as possible to each other.

In this context, it is advantageous that the sectors comprise the angles. This allows a very compact and narrow arrangement of the power supply(s) in a circle. In a first configuration the side walls of the first sectors of neighboring power supplies can be arranged basically parallel to each other, e.g. in a first circle. The side walls of neighboring housings can be in contact with each other or arranged with a small gap in between. Since the housings have advantageously at least a further sector, namely the second sector, that has side walls that are arranged with the second angle, the power supplies can also be arranged according to a second configuration. In other words, the power supplies may be arranged according to another circle that has diameter different from that of the first circle. In this second configuration the side walls of neighboring sectors can be again arranged basically parallel to each other.

Thus, a very compact and flexible arrangement can be achieved with one and the same housing. The sectors of the housing, wherein the side walls of the sectors are arranged in different angles, allow a very flexible and space effective arrangement of the power supplies. One and the same power supply can be used for several different machine applications, both applications with small carousels provided with few electron beam emitters and large carousels provided with many electron beam emitters.

Expediently, the first and the second angles are calculated as follows:
First angle=360/(2*maximum number of power supplies);
Second angle=360/(2*minimum number of power supplies).

If the minimum number of power supplies that shall be arranged in a circle, is for example 10, the second angle is 18°. If the maximum number of power supplies that shall be arranged in a circle (first circle) is for example 45, the first angle is 4°. It goes without saying that the side walls of the sectors of neighboring power supplies do not have to be arranged in parallel. Thus, e.g. 30 power supplies that have the aforementioned angles, can also be arranged in a circle. Possibly, none of the side walls of neighboring power supplies are parallel to each other in that case.

In one or more embodiments the housing comprises the plane of symmetry, wherein the plane of symmetry extends basically parallel to the vertical axis of the housing. If the power supply is arranged at a carousel, the plane of symmetry of the power supply basically crosses a centre of the carousel. In this case, the sectors taper towards the centre of the carousel or carrier plate. The vertical axis of the power supply is basically orientated perpendicular to the carousel or carrier plate. Expediently, the housing comprises a top wall and a bottom wall, wherein the bottom wall expediently comprises a high voltage output connector that is adapted for the already mentioned connection to the at least one electron beam emitter.

According to one or more embodiments, the first angle lies within a range of about 1 to 20°, wherein the second angle lies within a range of about 10 to 45°. In preferred embodiments the first angles lie within a range of about 3-5°, wherein the second angles lie within a range of about 15-19°. Preferably, the first angle measures about 4° and the second angle measures about 18°.

According to one or more embodiments the first sector comprises a first end portion and the second sector comprises a second end portion, wherein the first end portion is expediently formed by an outer side wall, and wherein the second end portion is formed by an inner side wall. Relating to the carousel or carrier plate, the second end portion is that side of the housing that is directed towards a centre point of the carousel or carrier plate, respectively. The first end portion is located oppositely. The plane of symmetry is orientated from the first end portion to the second end portion and vice versa. Alternatively, the second end portion may be formed by an edge. Alternatively, the second end portion may comprise a basically round shaped inner side wall. According to one or more embodiments, the side walls as well as the top and bottom walls can be made of metal, for example aluminum or steel. The walls can also be made of composite material that comprises different materials like plastic, metal, fibre reinforced material etc. According to one or more embodiments the housing is made of welded stainless steel, wherein the top end of the housing is expediently movable attached and sealed with appropriate o-rings. Alternatively or in addition, liquid gasket can be used. A detachable top end or in general a detachable part of the housing enables easy maintenance. According to one aspect of the invention the housing comprises at least one grip or handle that allows an easy transportation of the power supply. In addition, the power supply or the housing, respectively, comprises appropriate inlets or outlets, respectively, that allow e.g. a connection of a cooling system or an electric connection to other components.

Since the second angle is bigger than the first angle, the second end portion is generally smaller than the first end portion. This means that relating to the above mentioned carousel a very narrow arrangement of the power supplies is possible. Generally, the shape of the carousel is basically round, in particular circular. According to one or more embodiments of the invention the second end portion of the power supply is directed towards the centre of the carousel or of the carrier plate. It goes without saying that the available space on the carousel is restricted. In particular, if a plurality of power supplies shall be arranged in a circle at the carousel/carrier plate, a minimum diameter of the circle depends on the sizes or dimensions, respectively, of the houses. However, advantageously the power supply or the power supplies, respectively, comprise the second pair of side walls that is arranged in the second angle. As a consequence, the dimensions of the second end portion(s) are very small which enables a very small minimum diameter of the circle. In other words, a very compact arrangement is possible as the sectors of the power supplies taper towards the centre of the carousel or carrier plate. On the other side, as the first angle is smaller than the second angle a very big volume is provided by the housing for the arrangement of the electric system. In addition, the first angle is adapted for the arrangement of a plurality of power supplies in a circle that is preferably big and which allows the arrangement of a high number of power supplies.

According to one or more embodiments, the housing is filled with an insulation medium, in particular an insulation gas, such as nitrogen, halogen or vacuum. Nitrogen is a dielectric gas that is adapted to prevent a rapidly quench electric discharges. An advantage of the use of an insulation gas, such as nitrogen, contrary to the usage of e.g. insulation oil is that a gas cannot leak out and, for example, damage or pollute the material that has to be sterilized. Another big advantage is the low density of a gas contrary to a density of a liquid insulation material, such as oil. As already mentioned, the sterilization unit is in general arranged at carousels which rotate fast. The weight of the sterilization unit should therefore be minimized. This weight reduction can advantageously be realized by the usage of an insulation gas, such as nitrogen. To increase the insulation properties of the insulation gas, such as nitrogen, the insulation gas is, according to one or more embodiments, dried and/or pressurized. The pressure lies preferably within a range of about 2 to 3 bar, in particular within a range of about 2.5 bar (absolute pressure). In this context, it has to be mentioned that the housing of the power supply comprises according to one or more embodiments at least one electric insulation shield. The at least one electric insulation shield can be for example made of polyethylene, wherein the at least one insulation shield can be arranged in and/or at the housing of the power supply or in and/or at the wall(s) of the housing, respectively. The at least one insulation shield can reduce the risk of corona and electric discharges which have to be absolutely avoided as they can damage the power supply and its components. It goes without saying that in particular the people that work with the power supply or the sterilization device respectively have to be protected.

Expediently, the electric system of the power supply comprises power electronic components, high voltage components and control system components. According to one ore more embodiments, the outer design of the housing, comprising the at least two sectors, is also transferred to an inside design of the housing. This means that the housing comprises expediently a first and a second chamber, wherein the power electronic components and the control system components are located e.g. within the second chamber and wherein the high voltage components are arranged e.g. in the first chamber. In other words, the first chamber is at least partly formed by the first sector, wherein the second chamber is at least partly formed by the second sector. One of the high voltage components is for example a voltage multiplier that is adapted to multiply an input voltage up to the high voltage that is needed to operate the electron beam emitter. According to one or more embodiments, the first chamber comprises the already mentioned high voltage output connector.

According to one or more embodiments, at least one further pair of side walls is arranged between the first pair of side walls and the second pair of side walls, wherein an angle of the further pair of side walls lies preferably between the first angle and the second angle. In other words, an additional sector is located between the first sector and the second sector. Generally, the angle of the additional sector or the further pair of side walls respectively should lie within the first angle and the second angle. However, the angle of the side walls of the additional sector can be also smaller than for example the angle of the first sector. If necessary, also further additional sectors can be arranged.

According to another aspect of the invention there is provided a power supply device, in particular for a sterilization device, comprising a plurality of power supplies. Each power supply comprises a housing, wherein the housing comprises at least a first sector and a second sector. The first sector comprises a first pair of opposing side walls, and the second sector comprises a second pair of opposing side walls.

The plurality of power supplies is adapted to be arranged to form either a first configuration or a second configuration. The first configuration is a first circle and the second configuration is a second circle. In the first circle the side walls of the first sectors of neighboring power supplies are orientated basically parallel to each other. In the second circle the side walls of the second sectors of neighboring power supplies are orientated basically parallel to each other.

According to one or more embodiments the power supply system comprises a carrier plate, wherein the plurality of power supplies is arranged on the carrier plate. According to one or more embodiments, a carrier plate comprises at least two adjustment areas, wherein the two adjustment areas are basically circular and wherein a diameter of the first adjustment area is bigger than a diameter of the second adjustment area, wherein the plurality of power supplies is arrangeable or arranged, respectively, at the first adjustment area and/or at the second adjustment area. In other words, the plurality of power supplies can be arranged in a first circle and in a second circle, wherein the diameters of the circles are different. However, even though the design of the power supplies is always the same, the neighboring sides walls of the housings can be arranged basically parallel to each other in the first circle as well as in the second circle. According to one ore more embodiments, length of the side walls of the sectors that are measured along the side walls (and basically parallel to the circles or the carrier plate, respectively), are dimensioned so that transition regions of the first and the second sectors lie approximately on the first and the second circle. In addition, centre points of electron exit windows of electron beam emitters that are connected to the power supplies are positioned basically on the first and the second circle. However, according to one or more embodiments, the centre points of the electron exit windows can be also shifted with reference to the (first or second) circles, in particular radially shifted.

According to a further aspect of the invention a sterilization unit is provided. The sterilization unit comprises a power supply and at least one electron beam emitter. The power supply comprises a housing, wherein the housing comprises at least a first sector and a second sector. The first sector comprises a first pair of opposing side walls, and the second sector comprises a second pair of opposing side walls. The side walls are orientated basically parallel to a vertical axis of the housing. The first pair of side walls is arranged in a first angle and the second pair of side walls is arranged in a second angle, wherein the first angle and the second angle are different from each other.

The power supply according to the invention can include the features and advantages of the power supply device and of the sterilization unit according to the invention and vice versa.

Additional aspects and features of the current invention are shown in the following description of embodiments of the current invention with reference to the attached drawings. Single features or characteristics of respective embodiments are explicitly allowed to be combined within the scope of the current invention.

Figure 1:
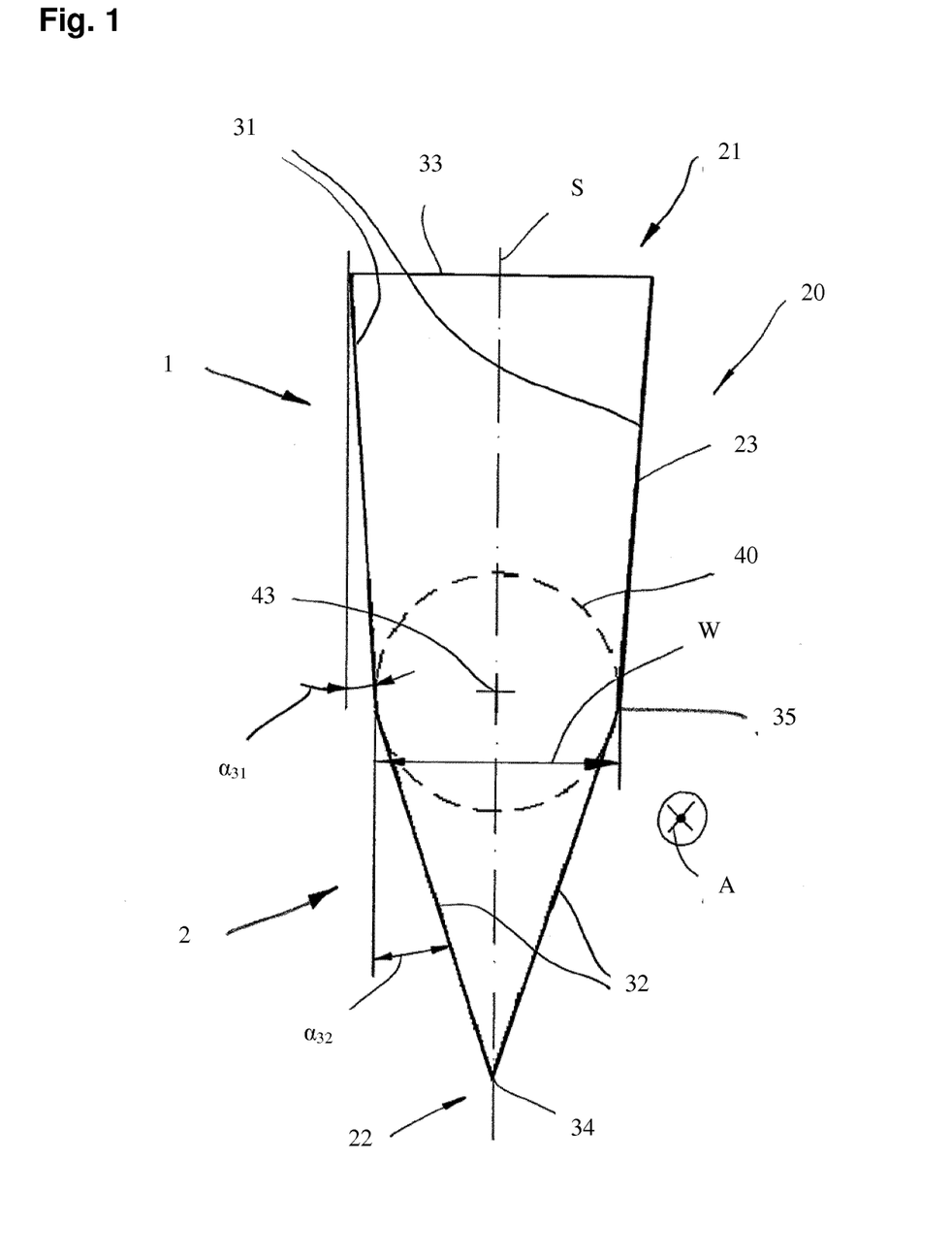
FIG. 1: shows an embodiment of a power supply in a top view.

Referring now to FIG. 1 an embodiment of a power supply 20 in a top view is shown. The power supply 20 comprises a housing 23 that comprises a first pair of side walls 31 and a second pair of side walls 32. The first pair of side walls forms a first sector 1, wherein the second pair of side walls 32 forms a second sector 2. The second sector 2 comprises a second end portion 22 that, in this embodiment, is formed as an edge 34. Other designs of end portions 22 will be described in relation to FIG. 7. The first sector 1 comprises a first end portion 21 that is formed by a wall 33. The first sector 1 is formed as a truncated triangle with the truncation facing the second sector 2.

A dotted circle indicates a position of an electron beam emitter 40. In particular, a cross within the dotted circle indicates a centre point 43 of an electron exit window of the electron beam emitter 40. According to one or more embodiments the housing 23 has a width w in this region that lies within a range of about 70 to 150 mm. In particular, a width w of about 110 mm can be suitable, wherein a diameter of the electron beam emitter 40 that is visualized by the dotted line measures about 110 mm.

The housing 23 is symmetric to a plane of symmetry S. The first pair of side walls 31 are angled an angle $\alpha_{31}$ in relation to the plane of symmetry S. The side walls 31 are inclined towards each other, i.e. towards the plane of symmetry S. The distance between the side walls 31 are smallest in a sector end being closest to the second sector. The angle $\alpha_{31}$ lies within a range of about 3 to 5 degrees. The second pair of side walls 32 are angled an angle $\alpha_{32}$ in relation to the plane of symmetry S. These side walls 32 are also inclined towards each other, i.e. towards the plane of symmetry S. The distance between the side walls 32 are largest in a sector end being closest to the first sector. The angle $\alpha_{32}$ lies within a range of about 17 to 19 degrees. This design can enable an optimal arrangement of at least 10 to 45 power supplies 20, e.g. on a carrier plate. The housing 23 extends along a vertical axis A, wherein the vertical axis A would be orientated basically perpendicular to the carrier plate if the power supply 20 is arranged on it.

Figure 2:
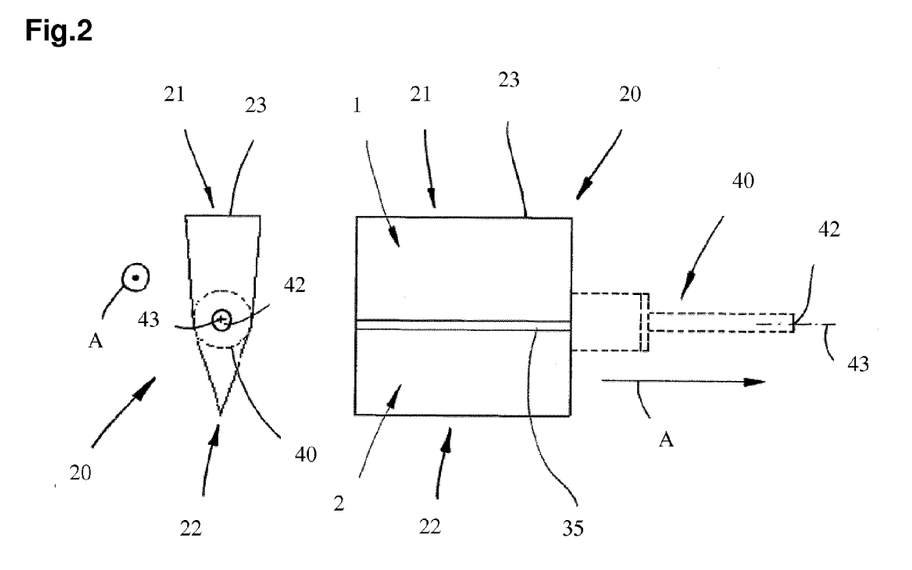
FIG. 2: shows an embodiment of a sterilization unit in a top view and a side view.

FIG. 2 shows on the left side a power supply 20 as already known from FIG. 1. However, a bottom side of the power supply 20 is shown so that an electron exit window 42 of an electron beam emitter 40 can be seen. On the right side of FIG. 2 the sterilization unit, i.e. an electron beam emitter and a power supply together, can be seen in a side view. First and second sectors 1, 2 are connected or combined by a transition region 35. The transition region 35 can be an edge or a radius which means that the transition from the first to the second sector can be e.g. seamless or not. The electron beam emitter 40 comprises two bodies, wherein the bigger body that is arranged at the power supply, e.g. via a high voltage output connector (not shown), has a diameter that lies e.g. within range of about 100 to 120 mm, e.g. within a range of about 110 mm. A smaller elongate body, that comprises an electron exit window 42, has a diameter that lies within a range of about 30 to 40 mm, e.g. within a range of about 35 mm. Reference numeral 43 indicated a centre of the electron exit window 42. The elongate body and at least one part of the bigger body comprise a vacuum or are formed as vacuum chambers. According to one or more embodiments an electron generator are located within the bigger body (not shown), within the vacuum. The electron generator is provided with a cathode housing and a filament. In use, an electron beam is generated by heating the filament. When an electrical current is set through the filament, the electrical resistance of the filament causes the filament to be heated to a temperature in the order of 2.000° C. This heating causes the filament to emit a cloud 44 (visible in FIG. 6) of electrons. The electrons are accelerated towards the electron exit window 42 by means of a high voltage potential between the cathode housing and the electron exit window 42. Subsequently, the electrons path through the electron exit window 42 and continue towards a target area, e.g. a part of the packaging material that has to be sterilized.

Figure 3A:
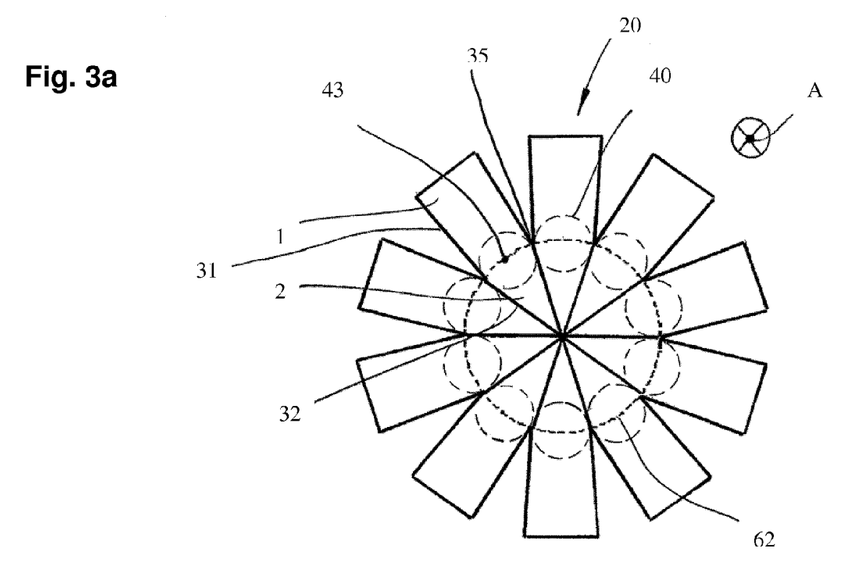
FIG. 3a: shows an arrangement of 10 power supplies of a power supply device in a top view.

FIG. 3a shows ten power supplies 20 in a top view and in a first configuration. In other words, a power supply device, or unit, is shown, wherein the power supplies 20 are arranged in a second circle 62. Electron beam emitters 40 or its positions, respectively, are indicated by dotted circles. As can be seen in FIG. 3a, side walls 32 of second sectors 2 of neighboring housings 23 are basically arranged parallel to each other. This is possible as angles $\alpha_{31}$ of first pairs of side walls 31 of first sectors 1 measure about 4°, wherein angles $\alpha_{32}$ of the second pairs of side 32 walls of the second sectors 2 measure about 18° (angles are not provided with reference signs, c. f. to FIG. 1). Centre points 43 of the electron beam emitters 40 lie expediently on the second circle 62. This first configuration may be used in for instance the application described in the international application No. PCT/EP2013/076870 filed by the applicant, in which a low number of electron beam emitters are used.

Figure 3B:
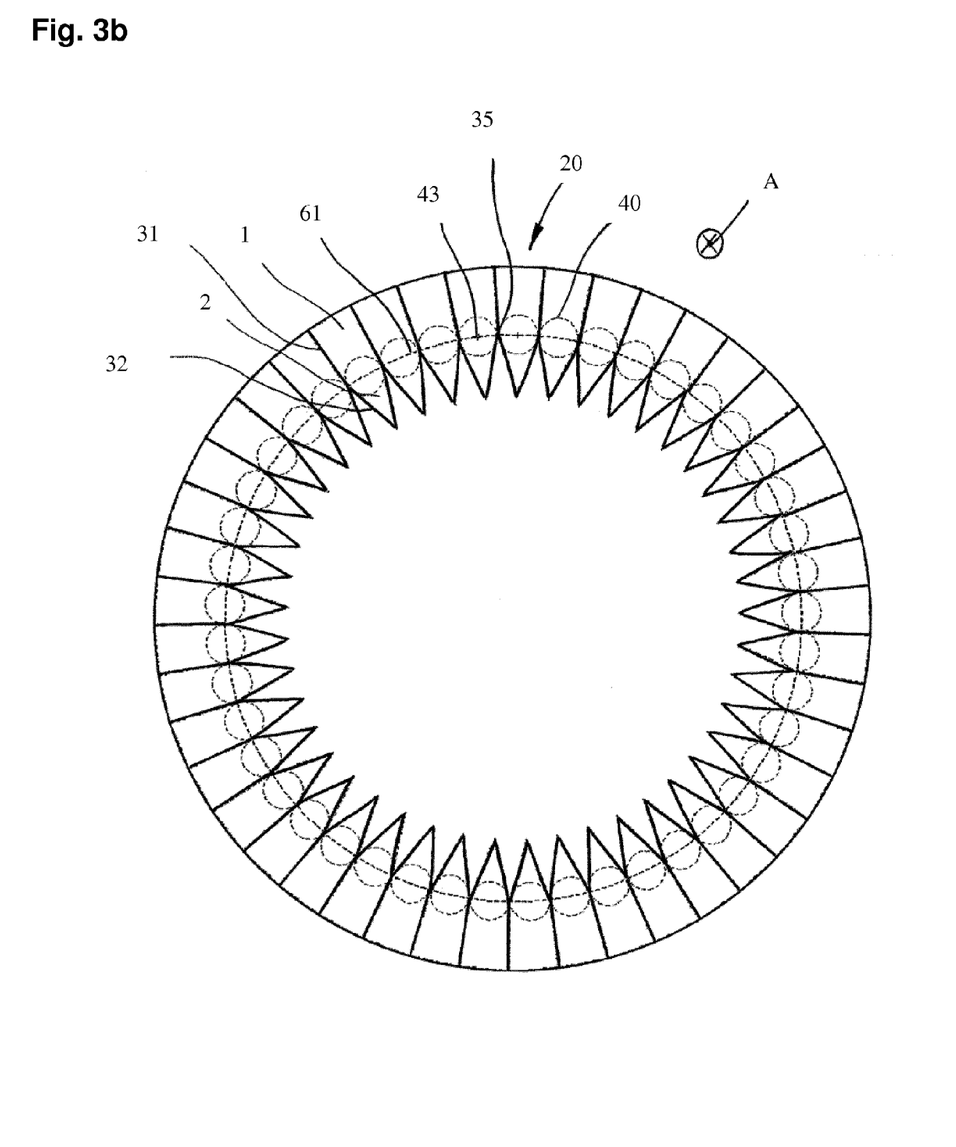
FIG. 3b: shows an arrangement of 45 power supplies of a power supply device in a top view.

In FIG. 3b, the same power supplies 20 as already known from FIG. 3a are arranged in a second configuration, wherein this configuration comprises 45 power supplies 20 that are arranged in a first circle 61. As can be seen from FIG. 3b, in this configuration the side walls 31 of the first sectors 1 of the power supplies 20 are arranged basically parallel to each other. This is possible as the angles $\alpha_{31}$ of the first pairs of side walls 31 of the first sectors 1 measure about 4°, wherein the angles $\alpha_{32}$ of the second pairs of side 32 walls of the second sectors 2 measure about 18° C. (angles are not provided with reference signs, c. f. to FIG. 1). Electron beam emitters 40 or its positions, respectively, are indicated by the dotted circles as already known from FIG. 3a. This second configuration may be used in large rotary filling systems, for example PET-bottling systems, in which there are traditionally many electron beam emitters present.

Figure 4A:
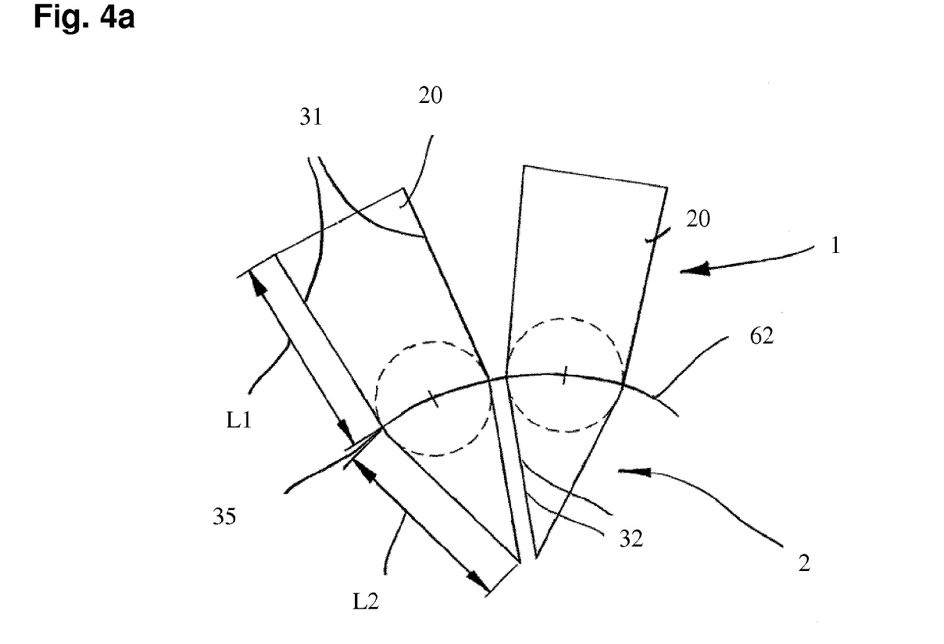
FIG. 4a: shows two power supplies of the arrangement of FIG. 3a in detail.
Figure 4B:
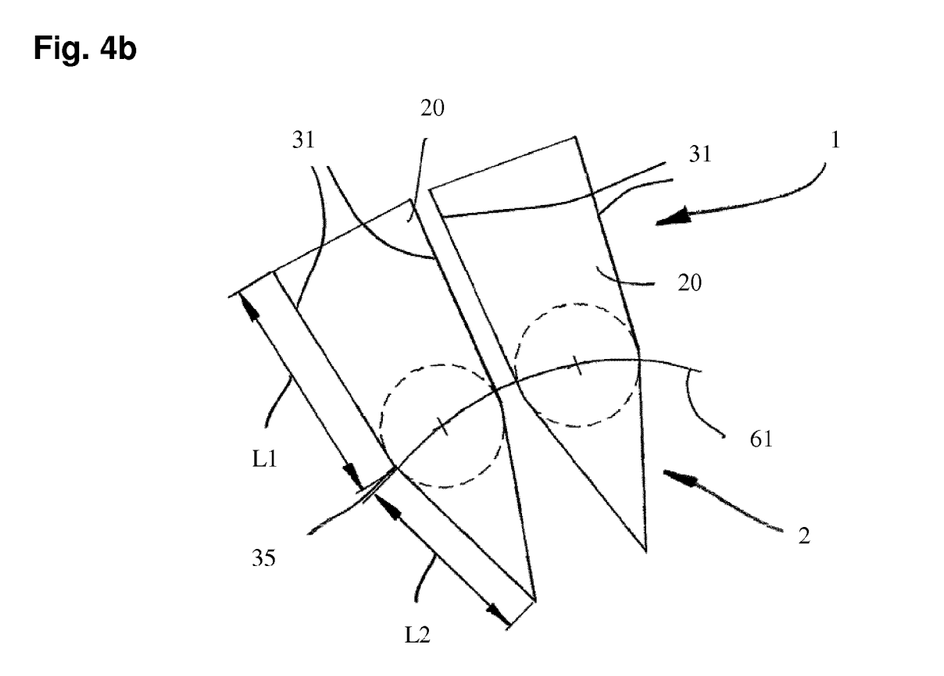
FIG. 4b: shows two power supplies of the arrangement of FIG. 3b in detail.

FIG. 4a and FIG. 4b show two power supplies of FIG. 3a and FIG. 3b in detail, in particular their positioning relatively to each other. It can be seen in FIG. 4a that the side walls 31 of the neighboring housings or power supplies 20, respectively, are arranged basically parallel to each other. In FIG. 4b the side walls 32 of the neighboring housings or power supplies 20, respectively, are arranged basically parallel to each other. Neighboring side walls 31, 32 can be in contact or not, if they are e.g. arranged at a carrier plate. Length L1 and L2 of the first and the second sectors 1 and 2 are designed in a way so that transition regions 35 are located basically on the first circle 61 or the second circle 62. In addition, also the centre points 43 of the electron beam emitters 40 are basically positioned or arranged on the first 61 or second circle 62, respectively. Thus, one and the same power supply 20 allows a very flexible arrangement.

Figure 5:
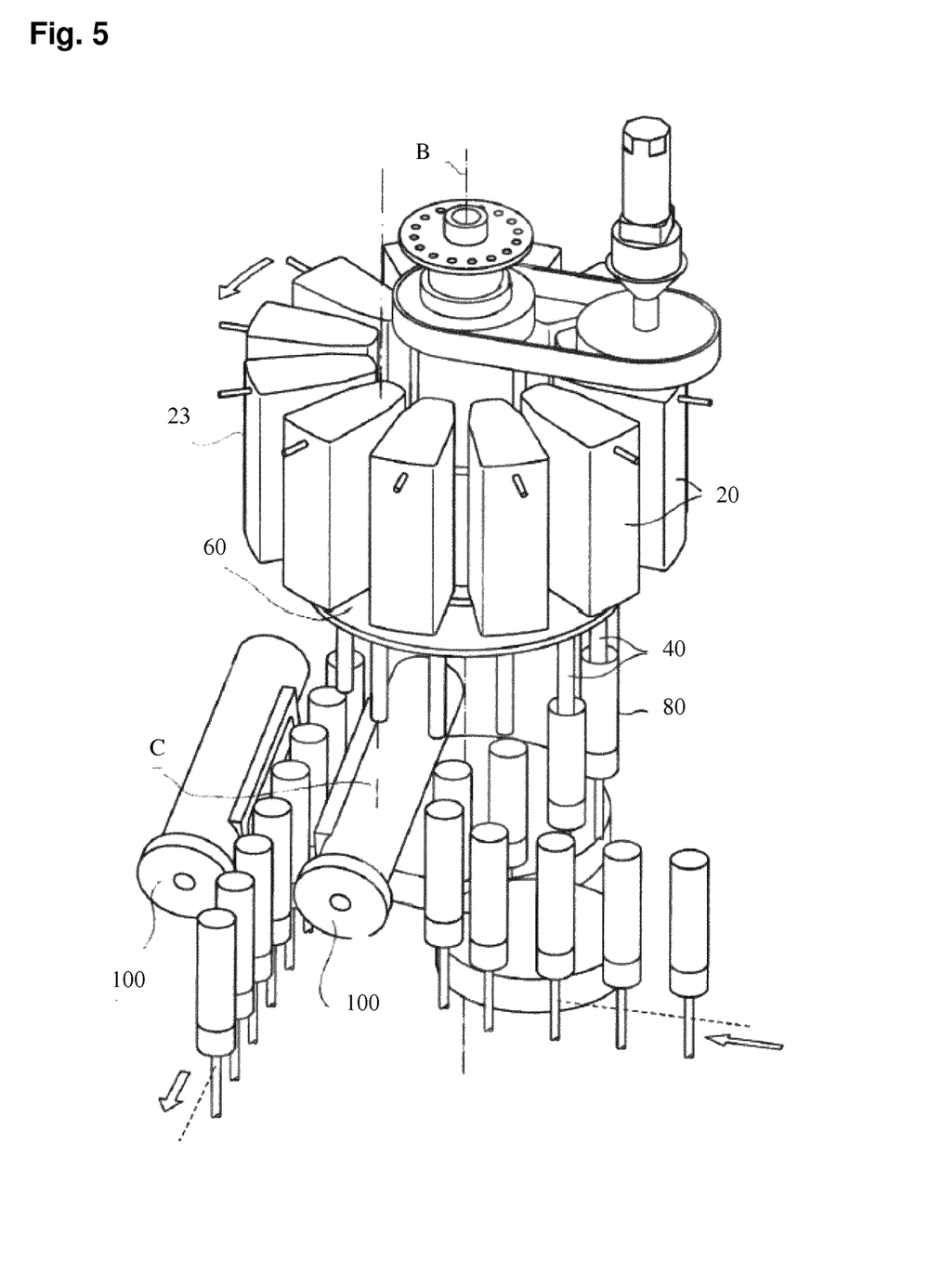
FIG. 5: shows a plurality of sterilization units arranged on a carrier plate.

FIG. 5 shows a sterilization device according to the international application No. PCT/EP2013/076870 filed by the applicant. A plurality of sterilization units of FIG. 2 is arranged on a carrier plate 60. Each sterilization unit extends along a vertical axis C. The axis C is parallel to a rotation axis B of the carrier plate 60. Each sterilization unit comprises a power supply 20 and an electron beam emitter 40. The sterilization units may be arranged in holes in the carrier plate 60. Packaging containers 80 are transported to the sterilization device for example via a conveyor positioned below the carrier plate 60. The packaging containers 80 reach the carrier plate 60 and are engaged with one of the (rotating) electron beam emitters 40 for interior surface sterilization. Movement directions are illustrated by arrows. During at least a part of one rotation of the carrier plate 60, the interior sterilization takes place and then the packaging container 80 is removed from the electron beam emitter 40. The packaging container 80 is then subsequently transported through an electron cloud provided in a gap between two large emitters 100 for outside surface sterilization.

Figure 6:
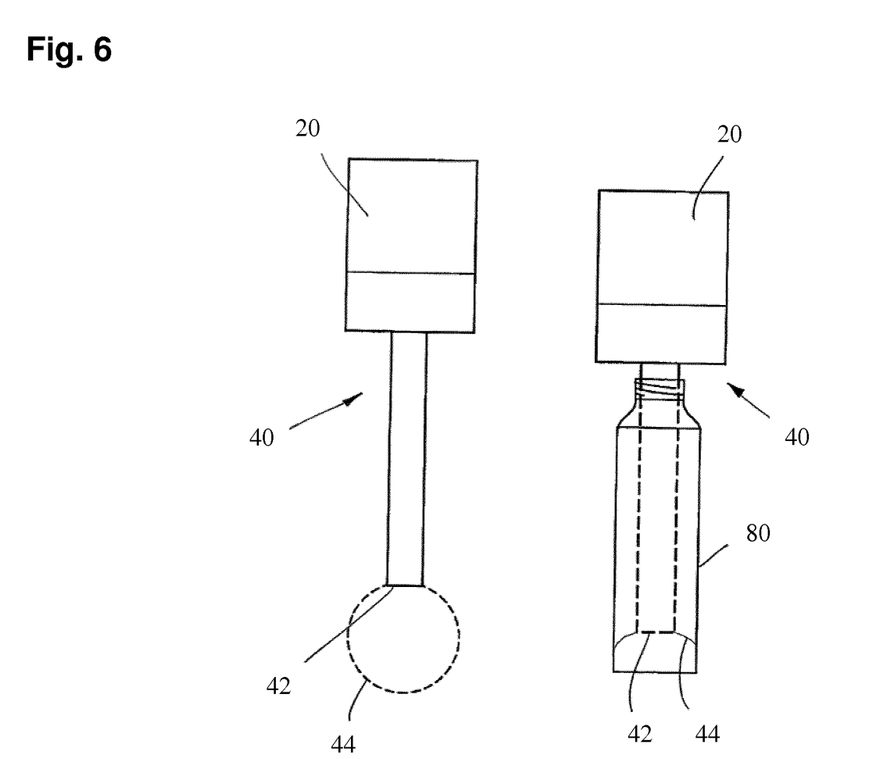
FIG. 6: shows an embodiment of a sterilization unit.

FIG. 6 shows a principle scheme of an embodiment of a sterilization unit comprising a power supply 20 and an electron beam emitter 40. The electron beam emitter 40 comprises an electron exit window 42, wherein an electron cloud 44 is formed during sterilization. The electron cloud 44 is for example used for inside sterilization of packaging material 80, in particular a packaging container 80, as can be seen on the right. Technical features of the electron beam emitter 40 as shown in FIG. 6 correspond to those explained with reference to FIG. 2.

Figure 7:
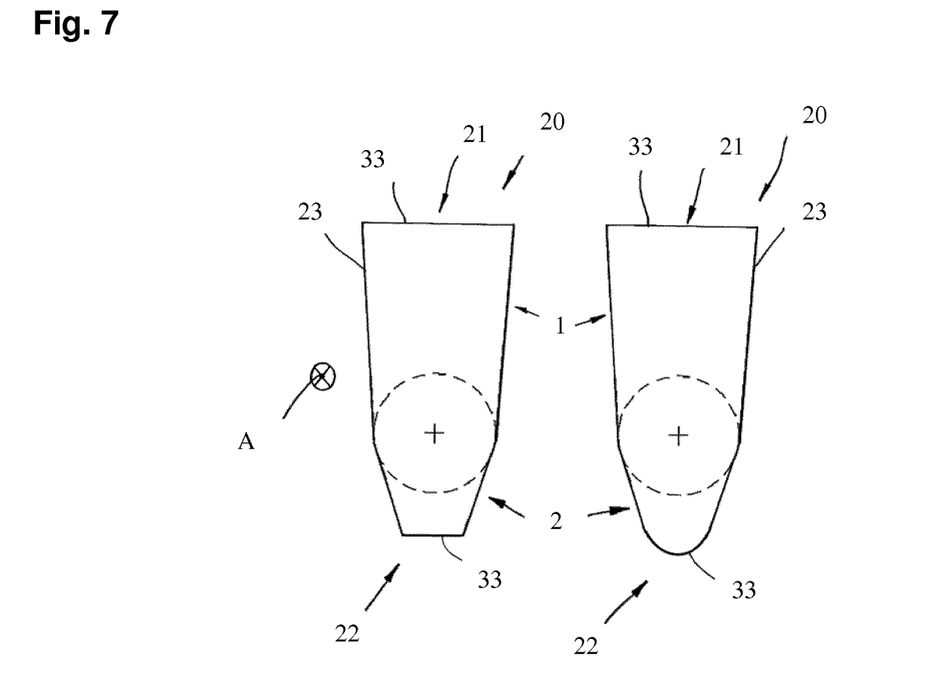
FIG. 7: shows two embodiments of a power supply in a top view.

FIG. 7 shows two embodiments of a power supply 20. The power supplies 20 in relation to FIGS. 1-6 have been shown with an end portion provided with an edge 34. However, different types/designs of second end portions 22 are shown. On the left side an end portion 22 is formed by a straight or flat wall 33, on the right side an end portion 22 is formed by a basically round shaped or curved wall 33. The shape of the end portion can be chosen depending on the application. The two embodiments in FIG. 7 are particularly suitable in applications where a drive axis is provided in the centre of the carrier plate. This can be realized when studying FIG. 5. The power supplies 20 of FIG. 5 are designed with a curved wall 33, similar to the right embodiment of FIG. 7.

REFERENCE NUMERALS 1 first sector
2 second sector
20 power supply
21 first end portion
22 second end portion
23 housing
31 first pair of side walls
32 second pair of side walls
33 (further) side wall
34 edge
35 transition region
40 electron beam emitter
42 electron exit window
43 centre point of electron exit window
44 (cloud) of electrons
60 carrier plate
61 first circle
62 second circle
80 packaging material
100 outside surface sterilization emitters
$\alpha_{31}$ angle of first pair of side walls
$\alpha_{32}$ angle of second pair of side walls
w width of the housing
L1 length of sector 1
L2 length of sector 2
S plane of symmetry
A vertical axis
B rotation axis
C vertical axis

The invention claimed is:

1. Power supply for a sterilization unit, comprising:
a housing,
the housing comprising at least a first sector and a second sector,
the first sector comprising a first pair of opposing side walls, and
the second sector comprising a second pair of opposing side walls,
the first pair of side walls being arranged in a first angle and the second pair of side walls being arranged in a second angle, and
the first angle and the second angle being different from each other.

2. Power supply according to claim 1, wherein the first angle is equal to 360° divided by two times a maximum number of power supplies, and wherein the second angle is equal to 360° divided by two times a minimum number of power supplies.

3. Power supply according to claim 1,
wherein the first sector comprises a first end portion, and wherein the second sector comprises a second end portion, wherein the first end portion is formed by a further side wall, and wherein the second end portion is formed by a further side wall.

4. Power supply according to claim 1, wherein the housing is filled with an insulation medium.

5. Power supply according to claim 1, wherein the housing comprises at least one electric insulation shield.

6. Power supply according to claim 1, wherein at least one further pair of side walls is arranged between the first pair of side walls and the second pair of side walls, wherein an angle of the further pair of side walls lies between the first angle and the second angle.

7. Power supply according to claim 1, wherein the first angle lies within a range of about 1-20°, and the second angle lies within a range of about 10-45°.

8. Power supply according to claim 1, wherein the housing is filled with an insulation gas.

9. Power supply according to claim 1, wherein the first sector is shaped as a truncated triangle as seen from a top view of the housing.

10. Power supply according to claim 9, wherein the opposing side walls of the first sector are angled towards one another so that the opposing side walls of the first sector approach one another in a direction towards the second sector.

11. Power supply according to claim 9, wherein the first angle is smaller than the second angle.

12. Power supply according to claim 9, wherein the housing is filled with an insulation medium.

13. Power supply according to claim 1, wherein the first angle lies within a range of about 1-20°, and the second angle lies within a range of about 10-45°, and the first angle is smaller than the second angle.

14. Power supply device, in particular for a sterilization device, comprising:
- a plurality of power supplies,
- each power supply comprising a housing,
- the housing comprising at least a first sector and a second sector,
- the first sector comprising a first pair of opposing side walls,
- the second sector comprising a second pair of opposing side walls,
- the plurality of power supplies being arranged in either a first circle, in which the side walls of the first sectors of neighboring power supplies are orientated parallel to each other, or a second circle, in which the side walls of the second sectors of neighboring power supplies are orientated parallel to each other.

15. Power supply device according to claim 14, comprising a carrier plate, wherein the plurality of power supplies is arranged on the carrier plate.

16. Power supply device according to claim 14, wherein each power supply is connectable to an electron beam emitter.

17. Sterilization unit for packaging material, the sterilization device comprising a power supply and at least one electron beam emitter,
- the power supply comprising a housing,
- the housing comprising at least a first sector and a second sector,
- the first sector comprising a first pair of opposing side walls,
- the second sector comprising a second pair of opposing side walls,
- the side walls are orientated basically parallel to a vertical axis of the housing,
- the first pair of side walls being arranged in a first angle and the second pair of side walls being arranged in a second angle,
- the first angle and the second angle being different from each other.

* * * * *